United States Patent [19]

Richard et al.

[11] Patent Number: 5,334,790
[45] Date of Patent: Aug. 2, 1994

[54] PROCESS AND CATALYST FOR PARTIALLY HYDROGENATING AROMATICS TO PRODUCE CYCLOOLEFINS

[75] Inventors: Michael A. Richard, Foster City; Jacques De Deken, Palo Alto; David K. Yee, Milpitas, all of Calif.

[73] Assignee: Catalytica, Mountain View, Calif.

[21] Appl. No.: 841,850

[22] Filed: Feb. 26, 1992

[51] Int. Cl.$^5$ .................................................. C07C 5/05
[52] U.S. Cl. ................................. 585/271; 585/266; 585/273; 585/274; 585/276
[58] Field of Search ............... 585/271, 273, 275, 277, 585/271, 266, 269; 502/302, 303

[56] References Cited

U.S. PATENT DOCUMENTS

| | | | |
|---|---|---|---|
| 3,912,787 | 10/1975 | Nowack et al. | 260/667 |
| 4,056,489 | 11/1977 | Hindin et al. | 252/462 |
| 4,079,097 | 3/1978 | Antos | 260/683.3 |
| 4,162,235 | 7/1979 | Acres et al. | 252/462 |
| 4,197,415 | 4/1980 | Hideyuki et al. | 585/23 |
| 4,235,755 | 11/1980 | Antos | 252/462 |
| 4,392,001 | 7/1983 | Don et al. | 585/269 |
| 4,495,373 | 1/1985 | Niwa et al. | 585/269 |
| 4,575,572 | 3/1986 | Ichihashi et al. | 585/266 |
| 4,665,274 | 5/1987 | Ichihashi et al. | 585/267 |
| 4,678,861 | 7/1987 | Mitsui et al. | 585/267 |
| 4,734,536 | 3/1988 | Nagahara et al. | 585/269 |
| 4,962,280 | 10/1990 | Tijburg et al. | 502/439 |

FOREIGN PATENT DOCUMENTS

| | | |
|---|---|---|
| 63-152333 | 6/1988 | Japan . |
| 0323192 | 7/1989 | European Pat. Off. . |
| 61-085334 | 4/1986 | Japan . |
| 62-045544 | 2/1987 | Japan . |
| 62-067033 | 3/1987 | Japan . |
| 62-081331 | 4/1987 | Japan . |
| 62-081332 | 4/1987 | Japan . |
| 62-108826 | 5/1987 | Japan . |
| 62-142126 | 6/1987 | Japan . |
| 62-205037 | 9/1987 | Japan . |
| 62-255438 | 11/1987 | Japan . |
| 62-294422 | 12/1987 | Japan . |
| 63-048232 | 2/1988 | Japan . |
| 63-088139 | 4/1988 | Japan . |
| 63-243038 | 10/1988 | Japan . |
| 63-243039 | 10/1988 | Japan . |
| 01-159059 | 6/1989 | Japan . |

OTHER PUBLICATIONS

Mizukami, F., "Partial hydrogenation of benzene to cyclohexene", *Senryo to yakuhin* 31:297–308 (1988).

Niwa et al., "Selective hydrogenation of benzene to cyclohexene with new ruthenium catalysts prepared by a chemical mixing procedure", *Journal of Molecular Catalysis* 34:247–249 (1986).

Niwa et al, "Partial hydrogenation of benzene wtih ruthenium catalysts prepared by a chemical mixing procedure: preparation and properties of the catalysts", *J. Chem. Tech. Biotechnol.* 36:236–246 (1986).

*Primary Examiner*—Anthony McFarlane
*Assistant Examiner*—P. Achutamurthy
*Attorney, Agent, or Firm*—Morrison & Foerster

[57] ABSTRACT

This is a catalyst and a process for partially hydrogenating polycyclic and monocyclic aromatic hydrocarbons such as benzene, naphthalenes, biphenyls, and alkylbenzenes to produce the corresponding cycloolefins. The catalyst is a hydrogenation catalyst comprising ruthenium on a composite support. It is a process in which the product cycloolefin is produced in high yield and with high selectivity.

31 Claims, 1 Drawing Sheet

PROCESS AND CATALYST FOR PARTIALLY HYDROGENATING AROMATICS TO PRODUCE CYCLOOLEFINS

FIELD OF THE INVENTION

This is a catalyst and a process for partially hydrogenating polycyclic and monocyclic aromatic hydrocarbons such as benzene, naphthalenes, biphenyls, and alkylbenzenes to produce the corresponding cycloolefins. The catalyst is a hydrogenation catalyst comprising ruthenium on a composite support. It is a process in which the product cycloolefin is produced in high yield and with high selectivity.

BACKGROUND OF THE INVENTION

Cycloolefins are materials useful in the production of other high value products. For instance, in the commercial production of the polyamide known as NYLON 66, cyclohexene is first converted to cyclohexanol. The cyclohexanol is then oxidized to adipic acid with nitric acid, converted to a salt, and finally converted to the polymer. Other members of the cycloolefin family have similar utility.

The previously used hydrogenation processes have fallen into two classes: one class consists of multistep processes starting with benzene or substituted benzenes and produces cyclohexanes or halocyclohexanes as intermediates. For instance, one such process involved the steps of hydrogenating benzene to form cyclohexane, oxidizing the cyclohexane to produce cyclohexanol, and dehydrating the cyclohexanol to produce cyclohexene. The other major multistep process involves the steps of halogenating benzene to produce a halobenzene, hydrogenating the resulting product to halocyclohexane, and dehydrohalogenating the halocyclohexane to cyclohexene.

The other class of processes is a single step synthesis in which monocyclic aromatics are only partially hydrogenated to form the corresponding cycloolefins. Ruthenium catalysts are often used in these processes.

U.S. Pat. No. 3,912,787 discloses a partial hydrogenation process for the production of cyclic olefins using an aqueous dispersion of a solid ruthenium containing catalyst promoted with a transition metal. The aqueous dispersion is maintained at an essentially neutral or acid pH condition. The catalyst may be supported on well known oxidic supports.

U.S. Pat. No. 4,079,097 to Antos shows a process for dehydrogenating hydrocarbons using composite catalysts of a combination of a platinum group component, a cobalt component, and a bismuth component all on a porous catalytic carrier.

U.S. Pat. No. 4,197,415 shows a process for selectively partially hydrogenating aromatic hydrocarbons to cyclic olefins by contacting the aromatic hydrocarbon with hydrogen and a ruthenium catalyst in an aqueous dispersion containing the salt of a phosphorous acid. The ruthenium catalyst may also be promoted by one of a large number of metals preferably, however, indium, copper, or silver.

U.S. Pat. No. 4,392,001 to Don et al. shows a process for the partial hydrogenation of an aromatic hydrocarbon in the gas phase using a ruthenium catalyst. The reaction takes place in the presence of water vapor.

U.S. Pat. No. 4,495,373 to Niwa et al. shows an improved catalyst system for the partial hydrogenation of an aromatic hydrocarbon compound in the liquid phase using an admixture of water and a ruthenium-containing solid catalyst. The catalyst is prepared by the hydrolysis gelation of a silicon or aluminum alkoxide in a solution containing a ruthenium compound such as ruthenium alkoxide. After gelation, the gelled material is dried. Copper may be included in the gel catalyst. The patent suggests that the resulting catalyst provides "improved catalyst activity and selectivity" in a partial hydrogenation of an aromatic compound over conventional ruthenium-containing catalysts prepared by later impregnation of a preformed silica gel carrier.

U.S. Pat. No. 4,575,572 to Ichihashi et al. also shows a process for partially hydrogenating aromatic hydrocarbons using a catalyst of ruthenium and at least one of iron, cobalt, silver, and copper supported on a barium sulfate carrier all in the presence of water.

U.S. Pat. No. 4,665,274 to Ichihashi et al. discloses a process for producing cycloolefins by partial hydrogenation of the corresponding aromatic hydrocarbon with hydrogen gas in the presence of water and a catalyst of ruthenium and one or more metals selected from iron, cobalt, silver, and copper supported on a barium sulfate carrier. The carrier also includes one or more of silica, titania, and alumina.

U.S. Pat. No. 4,678,861 to Mitsui et al (assigned to Asahi Kasei Kogyo K.K.) teaches a process for producing cycloolefins by partially hydrogenating a monocyclic aromatic hydrocarbon in the presence of a supported ruthenium catalyst comprising a rare earth element (apparently preferably lanthanum). The ruthenium may be present in an amount between 0.1 and 10% of the overall weight of the catalyst. The process is carried out in a multiphase reaction medium of water, hydrocarbon, catalyst, and hydrogen. The aqueous phase preferably is alkaline and contains dissolved ZnO or $Zn(OH)_2$.

U.S. Pat. No. 4,734,536 to Nagahara et al. shows a process for producing a cycloolefin by a partial hydrogenation of a monocyclic aromatic hydrocarbon using a neutral or acidic aqueous solution in the presence of a particulate hydrogenation catalyst of metallic ruthenium having an average crystallite size of 200 Å or less, zinc compound as a promoter, and at least one additive selected from the group of oxides, hydroxides, and hydrates of Zr, Hf, Ti, Nb, Ta, Cr, Fe, Co, Al, Ga, and Si.

Japanese Kokai 61-085,334 discloses the preparation of cycloolefin by partial hydrogenation of aromatic hydrocarbons using a ruthenium-silica catalyst which has been activated through the use of an aliphatic polyhydric alcohol.

Japanese Kokai 62-045544 (assigned to the Asahi Chemical Industry co.) teaches a process for the partial hydrogenation of monocyclic aromatic hydrocarbons in the presence of water, finely crystalline metallic ruthenium (desirably below 200 Å, most preferably below 100 Å) containing zinc, and an acid (preferably sulfuric acid) to form a solution having a pH between 2.0 and 6.5.

Japanese Kokai 62-067033 to Nagahara et al (assigned to the Asahi Chemical Industry Co.) teaches that the deactivation of Ru-impregnated $La(OH)_3$ catalysts in benzene partial hydrogenation reactions may be minimized by preventing the accumulation of Fe on the catalyst.

Japanese Kokai 62-081331 to Nagahara et al (assigned to the Asahi Chemical Industry co.) teaches that the deactivation of Ru-metal catalysts in benzene partial hydrogenation reactions using water as the reaction medium may be minimized by using reactors having walls of titanium or zirconium.

Japanese Kokai 62-081332 to Nagahara et al. (assigned to the Asahi Chemical Industry co.) teaches a process for the partial hydrogenation of monocyclic aromatic hydrocarbons in the presence of water, finely crystalline metallic ruthenium, and $ZrO_2$ or $HfO_2$.

Japanese Kokai 62-108826 (assigned to the Asahi Chemical Industry co.) teaches a process for the partial hydrogenation of monocyclic aromatic hydrocarbons in the presence of water, finely crystalline metallic ruthenium (desirably below 200 Å, most preferably below 100 Å), salts of Group IA or IIA metals (preferably zinc sulphate) and an acid (preferably sulfuric acid) to form a solution having a pH between 0.5 and 7.0.

Japanese Kokai 62-142126 to Ichihashi et al. (assigned to the Sumitomo Chemical Co.) teaches a process for the partial hydrogenation of monocyclic aromatic hydrocarbons in the presence of water, ruthenium on supports of Group IA alkali metal salts of phosphorous oxoacids, and salts of phosphorous oxoacids as additives (optionally, with a metal of iron, cobalt, nickel, copper, silver, or zinc—particularly zinc, aluminum, barium, and cobalt orthophosphate). An example showed 3.8% conversion of benzene and 50.8% selectivity to cyclohexene.

Japanese Kokai 62-205037 to Nagahara et al (assigned to the Asahi Chemical Industry co.) teaches a process for the partial hydrogenation of monocyclic aromatic hydrocarbons in the presence of water, finely crystalline metallic ruthenium (desirably below 200 Å most preferably below 100 Å), and solid basic zinc sulphate.

Japanese Kokai 62-255438 to Niwa et al (assigned to Fuji K.K. and the Agency of Industrial Science and Technology) suggests a process for partially hydrogenating an aromatic hydrocarbon in the presence of $H_2$ with a catalyst of ruthenium and copper prepared by dispersing those metals in a solid obtained from a metal hydroxide (preferably silica, alumina, or zirconia) colloid.

Japanese Kokai 62-294,422 assigned to Asahi Chemical Industries, K.K., shows a process for the partial hydrogenation of monocyclic aromatic hydrocarbons in the presence of water, a hydrogenating catalyst containing fine crystallite ruthenium, and a solid basic zinc sulfate. The conversion of benzene is said to be about 70% and the selectivity to cyclohexene is said to be 70% to 80%.

Japanese Kokai 63-048232 (assigned to the Asahi Chemical Industry Co.) teaches a process for the partial hydrogenation of monocyclic aromatic hydrocarbons in the presence of a ruthenium catalyst on a carrier, zinc oxide or hydroxide, and water containing an accelerator selected from salts of Group IA or IIA metals, manganese, zinc or cobalt.

Japanese Kokai 63-88139 to Nagahara et al. (assigned to the Asahi Chemical Industries Co.) shows a process for partially hydrogenating single ring aromatics using hydrogen in the presence of a neutral to acidic aqueous solution and a hydrogenation catalyst containing metallic ruthenium crystallites with a diameter of 200 Å or less, at least one separate metal hydroxide or hydrated metal oxide selected from Ti, Zr, Hf, Nb, Ta, Cr, Fe, Co, Al, Ga, and Si, and further containing at least one solid basic zinc salt.

Japanese Kokai 63-152333 (assigned to the Asahi Chemical Industry co.) teaches a process for the partial hydrogenation of monocyclic aromatic hydrocarbons in the presence of solid basic zinc compounds in neutral or acidic water and metallic ruthenium on a support (preferably gamma-alumina).

Japanese Kokai 63-243038 (assigned to the Asahi Chemical Industry co.) teaches a process for the partial hydrogenation of monocyclic aromatic hydrocarbons in the presence of zinc compounds in neutral or acidic water and finely crystalline metallic ruthenium (desirably between 30 Å and 200 Å, most preferably between 40 Å and 100 Å) on a support (preferably $ZrO_2$ or $HfO_2$).

Japanese Kokai 63-243039 (assigned to the Asahi Chemical Industry co.) teaches a process for the partial hydrogenation of monocyclic aromatic hydrocarbons in the presence of water; a hydrogenation catalyst of colloidal metallic ruthenium on a metal salt, hydroxide, or oxide support; and a soluble zinc compound.

Japanese Kokai 1-159,059 to Nagahara et al. shows a process for regenerating a ruthenium catalyst which has been used for partial hydrogenation of a cycloaromatic. The catalyst is regenerated by contacting the catalyst with oxygen or with sodium chlorite.

A Japanese publication entitled Senryotoyakuhin, 1986, 31 (11), 297–308 (Japan) discloses a process for preparing cyclohexene by partial hydrogenation of benzene. The reaction takes place in an aqueous medium at about 150° C. to 200° C. and 30 atmospheres to 70 atmospheres in the presence of a ruthenium catalyst and a copper, silver, or cobalt promoter.

Niwa et al. in a letter in the *Journal of Molecular Catalysis* (34, 1986) 247–249, entitled "Selective Hydrogenation of Benzene to Cyclohexene with New Ruthenium Catalyst Prepared by Chemical Mixing Procedure" discloses a process for partial hydrogenation of benzene using desirably a catalyst of ruthenium and copper on silica. The communication shows a cyclohexene yield of 31% and a benzene conversion of 83%.

Niwa et al. in *J. chem. Tech. Biotechnol.* 1986, 36, 236–246, shows the partial hydrogenation of benzene with a ruthenium catalyst prepared by a specific chemical mixing procedure. The catalysts are made by mixing ruthenium chloride and (optionally, copper chloride) with a diol such as ethylene glycol to form a solution of metal complexes. Tetraethoxysilane was added to the prior solution and water was added to hydrolyze the various metal alkoxides formed during the stirring. The material was then gelled and dried to form the catalyst.

Published European Patent Application 0,323,192 shows a hydrogenation catalyst prepared by adsorbing ruthenium ions on a hydrotalcite clay and then reducing the adsorbed ruthenium ions. The catalyst is said to be suitable for use in partly reducing monocyclic aromatic hydrocarbons to cyclohexene.

None of the cited references suggest a process for producing cyclic olefins using a ruthenium-based catalyst on a composite support. The catalyst and process of the present invention have several advantages over the prior art. The inventive process shows very high yields with very efficient catalysts. No supported catalyst in the prior art suggests such high yields. No unsupported or precipitated catalyst shows such high efficiencies or productivities (when measured on a ruthenium basis).

SUMMARY OF THE INVENTION

This invention is a catalyst and process for partially hydrogenating polycyclic or monocyclic aromatic hydrocarbons to produce the corresponding cycloolefins. The catalyst is a hydrogenation catalyst comprising ruthenium on an oxidic, preferably composite, support. It is a process in which the product cycloolefin is produced in high yield, with high selectivity, and with very high productivities and efficiencies based on ruthenium.

The process is a multiphase operation in which a gaseous hydrogen phase and the solid catalyst are intimately intermixed with two liquid phases: an aqueous phase and a hydrocarbon phase containing both feedstock and product hydrocarbons.

The catalysts comprise ruthenium metal on a composite oxidic support. A base oxide such as alumina or silica is at least partially surrounded by a minor amount of a second relatively low inherent surface area oxidic material. The second oxidic material may be selected from metal or semimetal oxides or a lanthanum-containing material of the formula:

where $x<1$, $z<1$ and $x+y+z=1$.

A catalyst promoter of certain Group IB, IIB, and VIII metals may be included in the aqueous phase during the reaction.

BRIEF DESCRIPTION OF THE DRAWINGS

The drawing is a graph showing the production of cyclohexene as a function of benzene conversion for one of the preferred catalysts.

DESCRIPTION OF THE INVENTION

Figure 1:
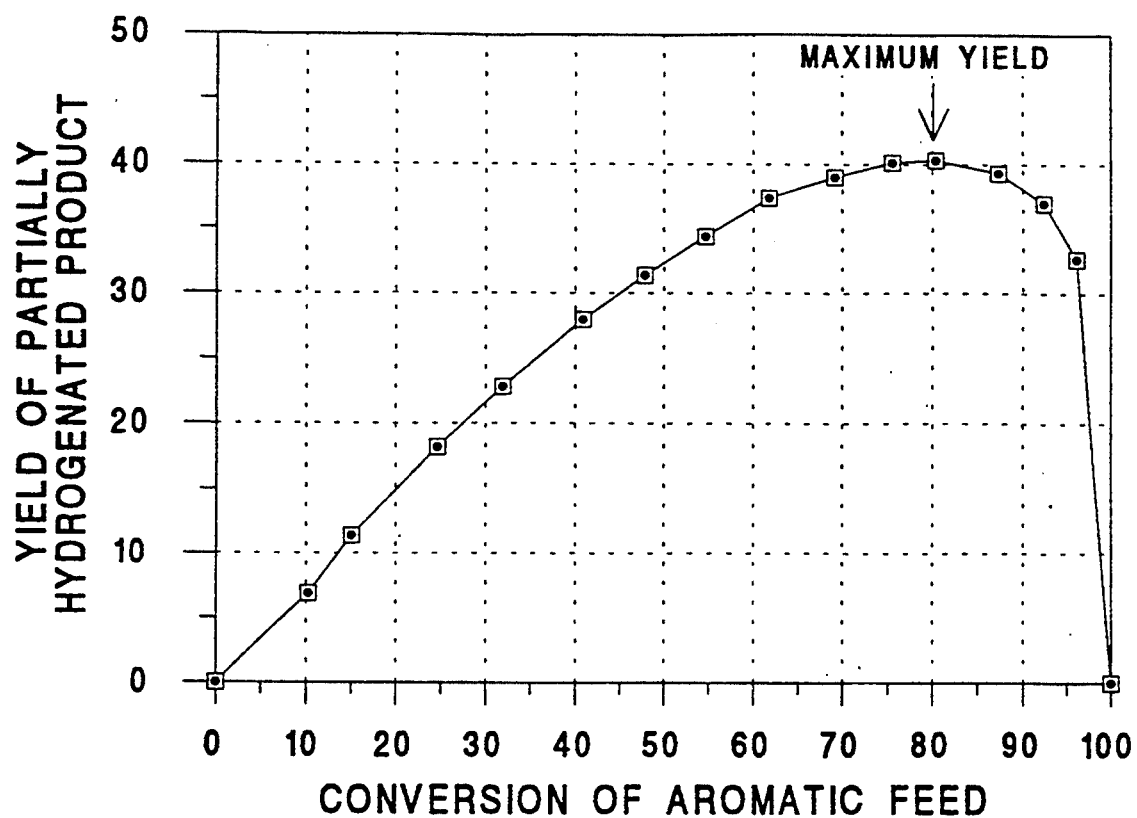

This is a catalytic process for partially hydrogenating poly- or monocyclic aromatic hydrocarbons to produce the corresponding cycloolefins. The aromatic feedstocks may be such materials as substituted or non-substituted naphthalenes or biphenyls, benzene, or alkylbenzenes such as toluene, o-, m-, p-xylene, ethylbenzene, or similar materials. The hydrogenation catalyst comprises ruthenium on a composite support. It is a process in which the product cycloolefin is produced in high yield, with high selectivity, and with very high productivities and efficiencies based on ruthenium.

FEEDSTOCKS

The feedstocks suitable for this partial hydrogenation process may comprise monocyclic aromatic hydrocarbons such as benzene and alkylbenzenes. Linear and branched alkylbenzene feedstocks may include compounds such as benzene, toluene, o-, m-, p-xylene, ethylbenzene, n-propylbenzene, cumene, butylbenzenes such as t-butylbenzene and isobutylbenzene, phenylcyclohexane, mesitylene; alkoxy-substituted benzenes such as anisole and phenetole; polyalkylene oxide-substituted benzenes such as polyethylene oxide phenyl ether, or polypropylene oxide phenyl ether; halogenated benzenes, such as fluorobenzenes, chlorobenzenes, bromobenzenes, iodobenzenes, and their o- and m- and p-substituted homologues; and similar aromatics and mixtures of any of the listed materials. Preferably the monocyclic aromatic compound is unsubstituted, or substituted with no more than one substituent such as an alkyl moiety. Most preferably the compound is benzene.

Other suitable feedstocks include polycyclic aromatic hydrocarbons which are substantially aromatic in character, i.e., the overall compound is not so fused or condensed as to lose its ability to act as an aromatic compound in classic chemical reactions in which aromatics take part. The aromatic rings in the polycyclic aromatic compounds may be fused or non-fused. The rings may be substituted at any position with alkyl or ether moieties, preferably, and if present, the substituents are alkyl in nature and contain 1–10 carbon atoms. Preferably, the polycylcic aromatic is unsubstituted or substituted with no more than two $C_2$ moieties. Examples of suitable polycyclic aromatic compounds are biphenyl, diphenyl ether, 4-phenoxy-1,1'-biphenyl, terphenyl, tetraphenyl, diphenylmethane, 1,2-diphenylethane, 1,3-diphenylpropane, methylbiphenyls, ethylbiphenyls, 3- or 4-isopropylbiphenyls, naphthalene, methylnaphthalenes, ethylnaphthalenes, beta-isopropylnaphthalenes, and similar naphthalenes. Preferably, the polycyclic aromatic compound is a $C_{12-24}$ compound. Most preferably the polycyclic aromatic compound are naphthalenes or biphenyls.

The feedstream may contain other hydrocarbon materials as well so long as they do not substantially interfere with the partial hydrogenation reaction. For instance, short chain linear and cyclic alkanes do not typically detract from the overall reaction and in some instances improve the overall productivity of the process.

CATALYSTS

The process employs a hydrogenation catalyst comprising ruthenium on a composite support.

Ruthenium is present in at least a catalytic amount, i.e., an amount at least suitable for causing a partial hydrogenation reaction to take place on an aromatic compound. Typically the catalyst need contain no more than about 20 % by weight ruthenium (based on the total weight of the ruthenium and the composite support) and preferably less than about 10% by weight and most preferably about 5–10% by weight. We have found that the catalyst contains ruthenium crystallites which are well dispersed and no more than about 25 Å in average diameter.

We have found that although the ruthenium catalyst works well without special regard to the method in which it is placed onto the support, if a specific procedure ("heat-soaking") is employed, the results are enhanced. That desired impregnation procedure involves dissolving a ruthenium compound such as ruthenium nitrosylnitrate or $RuCl_3$ hydrate in an acidic solution (preferably containing 1.0 % to 30 % HCl) and then holding the resulting solution at an elevated temperature (preferably between 70° C. and the boiling point of the solution) for a period of time sufficient to enhance the resulting catalyst's activity and stability. The solution, preferably after cooling, is then contacted with a suitable catalyst support and finally treated to dry the solid, reduce the ruthenium to its metallic form, and activate the catalyst (all as necessary for the process involved).

The composite support may comprise a major amount of a first relatively high specific surface area oxidic core material which is at least partially surrounded by a minor amount of a second relatively low inherent surface area oxidic material. The second oxidic material may be selected from metal or semimetal oxides or a lanthanum-containing material of the formula:

$$x(LaONO_3) + y(La_2O_3) + z(La(NO_3)_3)$$

where $x<1$, $z<1$ and $x+y+z=1$.

The specific surface area of the composite support is substantially higher than that of the second oxidic material. Very desirable oxidic core materials are high surface area (greater than about 50 m²/gm) silica, alumina, and silica-alumina. In particular, silica and transition phase aluminas such as eta or gamma phase materials or mixtures of the two are suitable.

The second oxidic material is either a metal or semimetal oxide having a low inherent surface area (less than about 10 m²/gm) or the lanthanum oxygen-nitrogen material mentioned above. Suitable metal or semimetal oxides include lanthanum oxide, zinc oxide, boria, ceria, zirconia, titania, or the like.

One preferred method of preparing a desired catalyst is the following procedure:

1. The high surface area oxidic core material is crushed and sieved to a powder with particle sizes in the range of 0.1 micron to 1 millimeter in diameter.
2. A salt precursor to the second oxidic material is loaded onto the oxidic core material from an aqueous solution by standard methods such as incipient wetness, adsorption, or others known to those skilled in the art.
3. The composite is calcined in air at 500°-1500° C. for 1-20 hours to convert the supported salt precursor to the oxide or to a mixture of oxide, nitrate, and oxynitrate.
4. A ruthenium salt solution is prepared by dissolving the ruthenium salt in water that preferably contains HCl; the acidic solution is heated to 80°-100° C. for about 1 hour; the acidic solution is cooled to room temperature.
5. A sufficient quantity of the acidic ruthenium solution to give the desired ruthenium loading is contacted with the composite oxide support to effect loading of the ruthenium onto the composite oxide support. It is preferred to adjust the concentration of the ruthenium salt in the acidic solution to the value required to give the desired loading in a volume of acidic solution approximately equal to incipient wetness volume of the composite oxide support. For ruthenium loadings above 7.5% this procedure is preferably carried out as a series of multiple loadings. For example, to prepare a catalyst that will contain 10% ruthenium, it is preferred to impregnate the composite oxide support in two steps with about 5% ruthenium being deposited in each step. The material is dried between loading steps.
6. The moist mass is dried.
7. The catalyst is produced by reducing the supported ruthenium salt. A preferred method for reducing the supported ruthenium salt is by heating at 200°-600° C. in flowing hydrogen for 1-20 hours. Other reduction methods and other reducing agents may be used.

The active catalyst comprises ruthenium particles supported on a composite support wherein the composite support has a BET surface area of at least 50 m²/gm and wherein a major fraction of the ruthenium particles are less than 25 Å in diameter.

PROCESS

The process of this invention entails using the noted catalyst in an amount of about 0.01% to about 50% of the weight of the aromatic to be partially hydrogenated. The amount of catalyst should be minimized, but 1% to about 20% should be adequate under most circumstances to perform the reaction. The amount of catalyst may also be varied depending upon the mode of operation desired and the desired overall reaction rate. By mode of operation, we mean that the process of partial hydrogenation may be carried out in a continuous or a discontinuous mode, in fixed bed, trickle bed or slurry reactors, in a batch, semi-batch, multiple batch reactions, or a continuous stirred tank reactor or a series of continuous stirred tank reactors. It is preferred to operate in a plug flow reactor mode, for example, fixed bed, trickle bed, or a series of continuous stirred tank reactors, rather than in a back mixed reactor mode as in a single stirred reactor, for example. The observed overall rate of conversion will generally increase with increasing ratio of catalyst to aromatic feed; however, since there are physical limitations imposed by the maximum rate of transfer of reactants to the catalyst, depending on the mode of operation and the extent of agitation, there will be a limit beyond which further addition of catalyst will not affect the overall rate of conversion of the aromatic feed. It is preferred to operate in a well mixed reactor with efficient agitation.

This process uses an inherently complex four-phase system: a gaseous hydrogen phase; an aqueous phase; a hydrocarbon phase containing aromatic feeds and partially and fully hydrogenated products; and the solid catalyst phase. The system is preferably operated in a mode which produces the maximum amount of partially hydrogenated products. The aqueous phase preferably contains a selectivity promoter. The promoter desirably is a sulfate or chloride salt of a Group VIII, IB, or IIB metal. Most preferred is cobalt sulfate. The concentration of the salt in the aqueous phase should be about 1-100 millimoles per liter. The concentration should be within a range to give the desired enhancement of selectivity to the partially hydrogenated aromatic product. The use of excessive amounts may be deleterious to the activity of the catalyst and, furthermore, at sufficiently high concentrations, there may be no selectivity benefit.

The ratio of the aqueous phase volume to the organic phase (aromatic plus products) volume is preferably at 1:1 or below 1:1. It is preferred to use the minimum amount of aqueous phase for a given volume of organic phase to reduce the required size of the reactor(s). The actual ratio will depend on the mode of operation. For continuous stirred tank reactors in series or as a single reactor, the preferred volume ratio is from 0.1:1 to 1:1. For trickle bed or fixed bed reactor modes of operation, the phase ratio is determined by factors other than reactor size. To effect turbulent flow in a trickle bed or fixed bed reactor, the volumetric flow of the aqueous phase can be much higher than the volumetric flow of the feed aromatic, wherein the volumetric flow of the feed aromatic is dependent upon the desired conversion per unit length of the reactor. In the specific case of a trickle bed reactor, the volumetric feed ratio of aqueous phase to aromatic feed will generally be greater than 5:1 and could be in the range of 5:1 to 100:1.

In the case of stirred tank reactors, either continuous, batch or semi-batch, it is preferred that the organic phase be the continuous phase with the aqueous phase being dispersed, under agitation, as small droplets within the continuous organic phase. The requirement is generally met when the volume ratio of aqueous phase to organic phase is at 1:1 or less than 1:1.

The concentration of selectivity promoter should be in the range of about 1-100 millimoles per liter. The actual concentration may be varied depending on the amount of catalyst used and, more specifically, the amount of ruthenium that is being used to catalyze the partial hydrogenation reaction. The molar ratio of selectivity promoter in the aqueous phase to ruthenium in the catalyst should be in the range of 0.1:1 to 50:1, the preferred range is 1:1 to 10:1, and more preferred is 1:1 to 3:1.

Upon contacting the reduced catalyst with the aqueous phase containing the promoter salt, the pH of the aqueous phase changes from near neutral to a value in the range of pH 3–6. It is preferred to operate the reaction at a pH in the range of 3–6.

In this process, partial hydrogenation may be carried out continuously or by batch. Although we prefer to use a continuous, stirred, multistage, series of reactors, other reactors employing suspended catalysts may be employed as may fixed or trickle beds. The reaction conditions are dependent in large measure upon the chosen form of the catalyst but in general we have found that the overall process pressure (hydrogen pressure plus the vapor pressure of the reactants, water, and products) should be between about 200 psig and 2000 psig, preferably between 300 psig and 800 psig. The reaction temperature should be between 100° C. and 200° C., preferably between 120° C. and 170° C.

In a typical reaction, hydrogen is fed "on demand"; that is, the hydrogen pressure is maintained at a constant value and hydrogen is continuously added to the reactor as it is consumed by the partial hydrogenation reaction. In certain reactor configurations it may be preferable to feed excess hydrogen through the reaction zone. In this particular mode of operation the excess volume of hydrogen acts as a stripping agent to remove products from the reaction zone in the vapor phase. A particularly preferred mode of operation includes flowing excess hydrogen at a sufficient rate to remove products from the reaction zone at the same molar rate as the feed rate of the aromatic compound being partially hydrogenated. By careful adjustments of the aromatic feed rate and the hydrogen flow rate, the residence time of the aromatic feed in the reaction zone may be controlled- This is an effective means of controlling the conversion in a continuous stirred tank reactor or in a series of continuous stirred tank reactors operated at steady state. This mode of operation greatly simplifies the operational difficulties inherent in modes of operation that require transfer and recycle of the aqueous catalyst slurry. By removing the products in the vapor phase, the solid catalyst remains in the reactor(s) and the need to pump a solids-containing slurry is eliminated. Some of the water in the reactor(s) is also removed through the stripping action of the excess hydrogen flow. This water may be recovered upon cooling and condensation of the vapor phase since the organic compounds form a separate liquid phase. The recovered water may be recycled to the reactor(s) to maintain the aqueous volume at a constant value. Optionally, this water may be discarded and fresh water used to make-up the aqueous volume in the reactor(s). While the ratio of hydrogen to aromatic is not a critical parameter, it is required that a sufficient volume of hydrogen be present in the reaction zone to allow for efficient mixing and dissolution of hydrogen in the organic and aqueous phases. This can be accomplished by maintaining a vapor volume in the reactor equal to 0.1 to 1 times the total liquid volume.

The productivity of the catalyst when used in the inventive process desirably is in the range of 10 to 500 pounds of partially hydrogenated aromatic product per pound of catalyst per hour, preferably 30 to 300 pounds of partially hydrogenated aromatic per pound of catalyst per hour.

EXAMPLES

The examples show the production of our inventive catalyst and the practice of our inventive process. Our conventions in discussing yield, conversion, selectivity, and the like in the following examples are as follows:

% Yield (Y)=(moles of cycloolefin produced/moles of aromatic feed) times 100

% Conversion (C)=(moles of aromatic feed converted/moles of aromatic feed) times 100

% Selectivity (S)=(moles of cyclooleifin produced/moles of aromatic hydrocarbon consumed) times 100

Productivity (P)=pounds of partially hydrogenated product per pound of catalyst per hour Maximum Yield of Partially Hydrogenated Product=(MAX-Y) is defined as shown in FIG. 1. The corresponding maximum conversion of aromatic feed is MAX-C.

Efficiency=pounds of partially hydrogenated product produced per pound of ruthenium used in the supported ruthenium catalyst per hour.

EXAMPLE 1

This example shows the preparation of a composite support of lanthanum oxide and lanthanum oxynitrate on silica. A 200 gm sample of powdered silica (Degussa Sipernat 22; average agglomerate size of 100 microns; surface area of 190 m$^2$/gm) was heated in air at 500° C. for 16 hours. A solution of 59.07 gm of La(NO$_3$)$_3$.6H$_2$O (Alfa) in 200 ml distilled water was prepared. After cooling the silica to room temperature, the aqueous solution of lanthanum nitrate was added dropwise with continuous mechanical mixing to load the silica pores. This incipient wetness loading method resulted in the formation of a free flowing material which was dried at 80° C. for 3 hours with intermittent mixing every 15 minutes during the first hour. The dried solid was heated in air at 500° C. for 16 hours. The nominal loading of lanthanum species, as weight percent lanthanum, was 9.5 wt. %. Infrared spectroscopic analysis confirmed the presence of nitrate in the sample. Thermal gravimetric analysis confirmed that the supported component consisted of a mixture of lanthanum oxide and lanthanum oxynitrate. The surface area of the composite support was about 130 m$^2$/gm.

EXAMPLE 2

This example shows the preparation of a catalyst of ruthenium on a composite support.

The catalyst of this example was prepared by the incipient wetness method using an incipient wetness volume of one milliliter per gram of composite support from Example 1. The desired loading was 10 wt. % ruthenium, thus the composite support was impregnated twice with sufficient solution to give 5 wt. % ruthenium per impregnation. A solution of 20% aqueous HCl was prepared by adding 237.8 milliliters of concentrated HCl to 202.2 milliliters of distilled water. The first impregnation solution was prepared by dissolving 25.85 gm of RuCl$_3$.xH$_2$O (Johnson Matthey, 44.8% ruthenium) in 220 milliliters of the 20% HCl solution. The solution was heated to 90° C. and held at 90° C. for one hour. After cooling to room temperature, the solution was added dropwise, with mechanical mixing, to 220 gm of the composite support from Example 1. The resulting free flowing material was dried at 80° C. with intermittent mixing every 15 minutes during the first hour. The dried material was cooled to room temperature and the incipient wetness loading procedure repeated with a second solution of 28.85 gm of $RuCl_3.xH_2O$ in 220 milliliters of 20% HCl that had been heated to 90° C., and held at 90° C. for one hour, and cooled to room temperature. The resulting free flowing material was dried at 80° C. with intermittent mixing every 15 minutes during the first hour. The active catalyst was generated by placing a quantity (2-5 gm) into a tubular reactor, purging the reactor with helium for 15 minutes at a flow of 2 standard liters per minute, switching to flowing hydrogen at 2 standard liters per minute, heating to 110° C. at 7° C. per minute, holding at 110° C. for 30 minutes, heating to 400° C. at 6° C. per minute, holding at 400° C. for 3 hours, and cooling to room temperature. The active catalyst was stored in an inert atmosphere glove box until use. Analysis of the ruthenium crystallite size using transmission electron microscopy showed that more than 90% of the well dispersed crystallites were smaller than 25 Å in diameter.

EXAMPLE 3

This example shows the use of the catalyst of Example 2 for the partial hydrogenation of benzene.

The catalyst (0.6 gm) was added to 150 cc of aqueous cobalt sulfate (7.1 millimoles per liter; pH of about 6.5-7.0) in a TEFLON-lined stirred tank reactor (0.7 liter volume) under an atmosphere of hydrogen at a total reactor pressure of 200 psig and at a temperature of 150° C. The catalyst suspension was stirred at 2000 rpm for one hour (pH changed to a value of about 4.5), at which time 250 cc of benzene (preheated to 150°) was added and the total pressure adjusted to 650 psig with hydrogen. Stirring was maintained at 2000 RPM and the pressure at 650 psig for the duration of the reaction; the pH remained at a value of about 4.5 during the course of the reaction. The liquid mixture in the reactor was sampled periodically and the composition was determined by a standard gas chromatographic method. The cyclohexene yield vs. benzene conversion is shown in the Figure. The maximum yield of cyclohexene was 40.3% at 80.4% conversion after a reaction time of 55 minutes. The selectivity to cyclohexene was 50.1%. The productivity was 169 pounds of cyclohexene per pound of catalyst per hour and the efficiency was 1690 pounds of cyclohexene per pound of ruthenium per hour.

EXAMPLE 4

This example shows the use of a lower mass of catalyst charge to the reactor.

In this example, 0.3 gm of the catalyst from Example 2 was used as in Example 3. The maximum yield of cyclohexene was 39.9% at 84.1% conversion after a reaction time of 90 minutes. The selectivity to cyclohexene was 47.4%. The productivity was 251 pounds of cyclohexene per pound of catalyst per hour and the efficiency was 2510 pounds of cyclohexene per pound of ruthenium per hour.

EXAMPLES 5-7

These examples demonstrate the effectiveness of the composite supported ruthenium catalyst for selective hydrogenation of toluene to a mixture of methylcyclohexenes, of biphenyl to cyclohexyl benzene, and of naphthalene to tetralin. For each feed or mixed feed, the reaction was carried out in a 500 cc Hastelloy C stirred tank reactor using 0.3 gm of the catalyst from Example 2 suspended in 150 cc of aqueous cobalt sulfate as in Example 4. All conditions of the reaction were identical to those in Example 4 except for the amount of aromatic feed.

Toluene

A mixture of 68.5 cc of benzene and 82.0 cc of toluene was fed to the reactor containing catalyst and aqueous cobalt sulfate. The maximum yield of cyclohexene was 34.4% and the maximum yield of the isomeric methylcyclohexenes was 36.0%.

Biphenyl

In a separate run, using a fresh sample (0.3 gm) of the catalyst from Example 2, biphenyl was partially hydrogenated to cyclohexylbenzene using the same procedure and conditions as for partial hydrogenation of toluene. After 163 minutes reaction time 72.5% of the biphenyl had been converted to cyclohexylbenzene with a selectivity of 98.6% and a yield of 71.5%. The other products were a mixture of 1-phenyl-1-cyclohexene, dicyclohexene, dicyclohexane, and cyclohexenylcyclohexane.

Naphthalene

A mixture of 5 gm of naphthalene in 150 cc benzene was used as the feed and was run as in the above examples with toluene and biphenyl. After two hours 95% of the naphthalene had been converted to tetralin; no other products derived from naphthalene were detected.

EXAMPLE 8 (COMPARATIVE)

This example demonstrates the comparatively poor performance of a ruthenium catalyst on a silica support that does not contain a second component (i.e., is not a "composite support") and which was prepared without HCl in the incipient wetness solution and without heating prior to impregnation of the support. Thus, 20 gm of powdered silica (Degussa Sipernat 22 as in Example 1) was heated at 500° C. in air for 16 hours. A solution of 2.35 gm $RuCl_3.xH_2O$ (Johnson Matthey, 44.8% ruthenium) in 20 ml of distilled water was prepared. This solution was used to impregnate 20 gm of silica by dropwise addition with continuous agitation. The free flowing mass was dried at 80° C. in air for 3 hours with mixing every 15 minutes during the first hour. A sample of the dried solid mass (10 gm) was impregnated a second time with a solution of 1.17 gm $RuCl_3.xH_2O$ in 10 ml distilled water to give a nominal loading of 10 wt. % ruthenium. The free flowing solid mass was dried at 80° C. for 3 hours. A sample of the dried powder was reduced in flowing hydrogen using the procedure used in Example 2. The reduced catalyst was stored in an inert atmosphere until use. Analysis of the ruthenium crystallite size using transmission electron microscopy showed that more than 90% of the crystallites were larger than 100 Å. When this catalyst (0.3 gm) was used to partially hydrogenate benzene by the procedure described in Example 4, very low productivity and low selectivities were observed as indicated by only 21.5% conversion after 180 minutes with a selectivity to cyclohexene of only 31.8% (6.9% yield).

EXAMPLE 9 (COMPARATIVE)

This example demonstrates the use of a silica supported ruthenium catalyst prepared as in Example 8 with two changes. First the ruthenium loading was reduced to 5 wt. % and the silica was impregnated one time; and, second, the added steps of using an aqueous solution of 20% HCl for the $RuCl_3 \cdot xH_2O$ and heating the solution to 90° C. for one hour. After cooling to room temperature, the silica support (15 gm) was impregnated by the incipient wetness method described in prior examples. The solid was dried and reduced as in prior examples. When this catalyst (0.3 gm) was used to partially hydrogenate benzene by the procedure of Example 4, very low productivity and low selectivities were observed as indicated by only 12.8% conversion after 180 minutes with a selectivity to cyclohexene of only 36.3% (4.7% yield).

EXAMPLE 10 (COMPARATIVE)

This example shows the benefit of using a composite support consisting of $La_2O_3$, $LaONO_3$, and $La(NO_3)_3$ on silica (as in Example 1) in comparison to silica alone as used in Example 8. A catalyst was prepared using the composite support of Example 1 and was doubly impregnated as in Example 2 except that the incipient wetness loading solutions of $RuCl_3 \cdot xH_2O$ in 20% HCl were not preheated to 90° C. for one hour. The catalyst was run as in Example 4 using 0.3 gm of catalyst. The maximum yield of cyclohexene was 33.0% at 72.7% conversion after a reaction time of 70 minutes. The selectivity to cyclohexene was 45.4%. The productivity was 298 pounds of cyclohexene per pound of catalyst per hour and the efficiency was 2980 pounds of cyclohexene per pound of ruthenium per hour. Although this example shows good productivity and efficiency for a catalyst prepared without using the preheat treatment for the incipient wetness loading solution, the catalyst is less effective (compared to catalysts prepared using the preheat step as demonstrated in Examples 3 and 4 using the catalyst from Example 2) due to the lower maximum yield of cyclohexene.

EXAMPLE 11 (COMPARATIVE)

This example shows the comparative performance of a catalyst comprising ruthenium on non-composite (lanthanum oxide) catalyst. A sample (10 gm) Of $La_2O_3$ was heated in air at 800° C. for 16 hours (surface area of 5.7 $m^2/gm$ characteristic of a low surface area oxide). The support was impregnated by the incipient wetness method, described in prior examples, using 5 ml of 20% HCl into which 1.17 gm of $RuCl_3 \cdot xH_2O$ had been dissolved and after heating the solution to 90° C. for one hour and then cooling to room temperature. After reduction, the catalyst (0.3 gm) was evaluated according to the procedure described in Example 4. Very low productivity and low selectivities were observed as indicated by only 9.1% conversion after 180 minutes with a selectivity to cyclohexene of 51.4% (4.7% yield).

EXAMPLE 12-14

These examples demonstrate the preparation and performance of catalyst prepared using ruthenium nitrosyl nitrate in place of ruthenium trichloride hydrate.

EXAMPLE 12

This example is analogous to Example 8. Silica was heated in air at 500° C. for 16 hours. After cooling to room temperature, 13.9 gm of silica was impregnated with an aqueous solution of $Ru(NO)(NO_3)_3$ (5.0 gm in 13.9 ml distilled water). The free flowing solid was dried at 80° C. for 3 hours with stirring every 15 minutes during the first hour. The dried solid was reduced in flowing hydrogen and the active catalyst was stored in an inert atmosphere until use. Note that the use of the nitrosyl nitrate salt of ruthenium allowed for preparation of this 10 wt. % Ru catalyst in a single impregnation. A sample of the active catalyst (0.3 gm) was evaluated by the procedure described in Example 4. The maximum yield of cyclohexene was 16.6% at 67.4% conversion after a reaction time of 105 minutes. The selectivity to cyclohexene was 24.7%. The productivity was 108 pounds of cyclohexene per pound of catalyst per hour and the efficiency was 1080 pounds of cyclohexene per pound of ruthenium per hour.

EXAMPLE 13

This example demonstrates improved performance when a composite support is used.

A catalyst was prepared by the method of Example 12 with the exception that the support used was the composite support from Example 1. A sample of the active catalyst (0.3 gm) was evaluated by the procedure described in Example 4. The maximum yield of cyclohexene was 26.0% at 74.0% conversion after a reaction time of 55 minutes. The selectivity to cyclohexene was 35.2%. The productivity was 294 pounds of cyclohexene per pound of catalyst per hour and the efficiency was 2940 pounds of cyclohexene per pound of ruthenium per hour.

EXAMPLE 14

This example demonstrates the use of a composite support and the added steps of using $Ru(NO)(NO_3)_3$ in 20% HCl as the incipient wetness loading solution, heating the incipient wetness loading solution to 90° C. for one hour, and cooling to room temperature prior to loading the composite support from Example 1 in a single impregnation step to give a nominal loading of 10 wt. % ruthenium in the active catalyst. A sample of the active catalyst (0.3 gm) was evaluated by the procedure described in Example 4. The maximum yield of cyclohexene was 35.1% at 83.2% conversion after a reaction time of 70 minutes. The selectivity to cyclohexene was 42.2%. The productivity was 277 pounds of cyclohexene per pound of catalyst per hour and the efficiency was 2770 pounds of cyclohexene per pound of ruthenium per hour. This example and Example 13 demonstrate that the use of the composite support results in high productivities and high efficiencies; this example shows that higher maximum yield is the primary benefit of using aqueous HCl with 90° C. preheating as the incipient wetness loading solution.

This invention has been shown both by description and by example. The examples are however only examples; they should not be used in any fashion to limit the scope of the invention otherwise described here.

Additionally, it should be clear that one having ordinary skill in this art would envision equivalents to the processes found in the claims that follow and that these equivalents would be within the scope and spirit of the claimed invention.

We claim as our invention:

1. A process for producing cycloolefins from aromatic feedstocks comprising the steps of:
    contacting hydrogen, an aqueous solution which contains a promoter selected from the group consisting of a Group VIII, IB, and IIB metal salt, and the aromatic feedstock comprising one or more monocyclic or polycyclic aromatic hydrocarbons with a partial hydrogenation catalyst to hydrogenate partially the aromatic feedstock and produce the corresponding cycloolefin, wherein the hydrogenation catalyst is comprised of ruthenium and a composite catalyst support made up of a core of a first oxidic material having a surface area greater than about 50 m²/gm which is at least partially surrounded by a second oxidic material having a surface area less than about 10 m²/gm, wherein the composite support has a BET surface area of at least 50 m²/gm, the ruthenium exists as particles no more than about 25 Å in average diameter, and the second oxidic material is selected from the group consisting of metal oxides, semimetal oxides, and a lanthanum-containing material of the formula:

$$x(LaONO_3) + y(La_2O_3) + z(La(NO_3)_3)$$

where $x<1$, $z<1$, and $x+y+z=1$; and separating the cycloolefin from the hydrogenation catalyst.

2. The process of claim 1 where the aromatic feedstock comprises benzene, alkylbenzenes, or mixture thereof.

3. The process of claim 2 where the aromatic feedstock comprises benzene.

4. The process of claim 2 where the aromatic feedstock comprises at least one alkylbenzene selected from the group consisting of toluene, o-xylene, m-xylene, p-xylene, ethylbenzene, propylbenzene, isopropylbenzene, butylbenzene, t-butylbenzene, and isobutylbenzene.

5. The process of claim 1 where the aromatic feedstock comprises one or more fused or non-fused polycyclic aromatic compounds.

6. The process of claim 5 where the polycyclic aromatic compound is selected from the group consisting of naphthalenes and biphenyls.

7. The process of claim 1 where the first oxidic material is selected from the group consisting of silica, alumina, and silica-alumina.

8. The process of claim 1 where the second oxidic material is one or more metal or semimetal oxides selected from the group consisting of lanthanum oxide, zinc oxide, boria, ceria, zirconia and titania.

9. The process of claim 1 where the ruthenium in the hydrogenation catalyst is introduced onto the catalyst support by a heat soaked acidic RuCl₃ solution.

10. The process of claim 1 where the ruthenium in the hydrogenation catalyst is introduced onto the catalyst support by a heat soaked acidic RuCl₃ solution.

11. The process of claim 1 where the promoter is a cobalt salt.

12. The process of claim 11 where the pH of the aqueous solution is between 3 and 6.

13. The process of claim 1 where the volume ratio of the aqueous solution to the aromatic feedstock and cycloolefins is 1:1 or less.

14. The process of claim 13 where the volume ratio is 0.1:1 to 1:1 and the process is operated in stirred tank reactors in series or in a single stirred tank reactor.

15. The process of claim 1 where the volume ratio of the aqueous solution to the aromatic feedstock and cycloolefin is greater than 5:1.

16. The process of claim 15 where the process is operated in a trickle bed reactor.

17. A process for producing cycloolefins from aromatic feedstocks comprising the steps of:

contacting hydrogen, an aqueous solution which contains a promoter selected from the group consisting of a Group VIII, IB, and IIB metal salt, and the aromatic feedstock with a partial hydrogenation catalyst to partially hydrogenate the aromatic feedstock and produce the corresponding cycloolefin, wherein the hydrogenation catalyst is comprised of no more than about 20% by weight of ruthenium and a composite catalyst support made up of a core of a first oxidic material having a surface area greater than about 50 m²/gm which is at least partially surrounded by a second oxidic material having a surface area less than about 10 m²/gm, wherein the composite support has a BET surface area of at least 50 m²/gm, the ruthenium exists as particles no more than about 25 Å in average diameter, and the second oxidic material is a lanthanum-containing material of the formula:

$$x(LaONO_3) + y(La_2O_3) + z(La(NO_3)_3)$$

where $x<1$, $z<1$, and $x+y+z=1$; and separating the cycloolefin from the hydrogenation catalyst.

18. The process of claim 17 where the aromatic feedstock comprises benzene, alkylbenzenes, or mixture thereof.

19. The process of claim 18 where the aromatic feedstock comprises benzene.

20. The process of claim 18 where the aromatic feedstock comprises at least one alkylbenzene selected from the group consisting of toluene, o-xylene, m-xylene, p-xylene, ethylbenzene, propylbenzene, isopropylbenzene, butylbenzene, t-butylbenzene, and isobutylbenzene.

21. The process of claim 17 where the aromatic feedstock comprises one or more fused or non-fused polycyclic aromatic compounds.

22. The process of claim 21 where the polycyclic aromatic compound is selected from the group consisting of naphthalenes and biphenyls.

23. The process of claim 22 where the first oxidic material is selected from the group consisting of silica, alumina, and silica-alumina.

24. The process of claim 23 where the first oxidic material is silica.

25. The process of claim 24 where the ruthenium in the hydrogenation catalyst is introduced onto the catalyst support by a heat soaked acidic RuCl₃ solution.

26. The process of claim 25 where the promoter is a cobalt salt.

27. The process of claim 26 where the pH of the aqueous solution is between 3 and 6.

28. The process of claim 19 where the volume ratio of the aqueous solution to the aromatic feedstock and cycloolefins is 1:1 or less.

29. The process of claim 28 where the volume ratio is 0.1:1 and 1:1 and the process is operated in stirred tank reactors in series or in a single stirred tank reactor.

30. The process of claim 17 where the volume ratio of the aqueous solution to the aromatic feedstock and cycloolefin is greater than 5:1.

31. The process of claim 30 where the process is operated in a trickle bed reactor.

* * * * *